US011389341B2

(12) United States Patent
Coates

(10) Patent No.: US 11,389,341 B2
(45) Date of Patent: Jul. 19, 2022

(54) INCONTINENCE PANT AND INCONTINENCE PANT SYSTEM

(71) Applicant: Tailored Technologies, Inc., Winston-Salem, NC (US)

(72) Inventor: Fredrica V. Coates, Winston-Salem, NC (US)

(73) Assignee: Tailored Technologies, Inc., Winston-Salem, NC (US)

( * ) Notice: Subject to any disclaimer, the term of this patent is extended or adjusted under 35 U.S.C. 154(b) by 0 days.

(21) Appl. No.: 16/743,513

(22) Filed: Jan. 15, 2020

(65) Prior Publication Data
US 2021/0212866 A1    Jul. 15, 2021

(51) Int. Cl.
*A61F 13/49*    (2006.01)

(52) U.S. Cl.
CPC .. *A61F 13/49061* (2013.01); *A61F 13/49006* (2013.01); *A61F 13/49011* (2013.01); *A61F 13/49014* (2013.01)

(58) Field of Classification Search
CPC .......... A61F 13/49061; A61F 13/49011; A61F 13/49006; A61F 13/49014; A61F 13/15; A61F 13/505; A61F 13/49446; A61F 2013/00225; A61F 2013/53463; A61F 2013/4944; D10B 2403/0213; D10B 2403/0223; A45C 2003/002; A41B 13/00
See application file for complete search history.

(56) References Cited

U.S. PATENT DOCUMENTS

| | | | | |
|---|---|---|---|---|
| 4,808,176 A * | 2/1989 | Kielpikowski | ... | A61F 13/49011 604/385.29 |
| 4,846,825 A * | 7/1989 | Enloe | ................ | A61F 13/49011 604/385.22 |
| 5,707,364 A * | 1/1998 | Coates | .............. | A61F 13/49004 604/385.01 |
| 6,117,121 A * | 9/2000 | Faulks | .............. | A61F 13/49017 604/385.29 |
| 6,895,603 B2 * | 5/2005 | Coates | .................. | A61F 13/495 2/238 |
| 2004/0243089 A1 * | 12/2004 | Veith | .................... | H04L 12/4641 604/385.22 |
| 2005/0210560 A1 * | 9/2005 | Coates | .................. | A61F 13/495 2/106 |
| 2008/0215027 A1 * | 9/2008 | Labit | ................. | A61F 13/49014 604/378 |

(Continued)

OTHER PUBLICATIONS

Definition of Pocket (Year: 2020).*

(Continued)

*Primary Examiner* — Quang D Thanh
*Assistant Examiner* — Gabriella E Burnette
(74) *Attorney, Agent, or Firm* — Suiter Swantz pc llo

(57) ABSTRACT

An incontinence pant including a main body having a front portion, a back portion, a crotch portion, a waist opening, and two leg openings. An elasticized waist cuff is formed at the waist opening and an elasticized leg cuff is formed at each of the two leg openings. Suspended mesh lining is disposed within the main body and is attached at each of the elasticized waist cuff and the two elasticized leg cuffs. The elasticized cuffs each have a pocket depth of at least 1 inch to form an absorbent area receiving a portion of an absorbent pad to capture leaked fluid.

12 Claims, 13 Drawing Sheets

(56) References Cited

U.S. PATENT DOCUMENTS

| | | | | |
|---|---|---|---|---|
| 2009/0216209 A1* | 8/2009 | Ekstrom | A61F 13/5644 | 604/367 |
| 2011/0178492 A1* | 7/2011 | Coates | A61F 13/5655 | 604/385.101 |
| 2012/0116339 A1* | 5/2012 | Labit | A61F 13/5644 | 604/372 |
| 2012/0116340 A1* | 5/2012 | Labit | A61F 13/493 | 604/377 |
| 2012/0116345 A1* | 5/2012 | Dime | A61F 13/49006 | 604/396 |
| 2012/0330264 A1* | 12/2012 | Lawson | A61F 13/49017 | 604/385.3 |
| 2014/0221954 A1* | 8/2014 | Wang | A61F 13/505 | 604/385.14 |
| 2014/0257231 A1* | 9/2014 | Wang | A61F 13/505 | 604/394 |
| 2014/0378936 A1* | 12/2014 | Coates | A61F 13/505 | 604/396 |
| 2015/0011957 A1* | 1/2015 | Cloutier | A41D 10/00 | 604/377 |
| 2015/0065979 A1* | 3/2015 | Coates | A61F 13/49004 | 604/371 |
| 2015/0157513 A1* | 6/2015 | Hovey | A61F 13/49006 | 604/385.15 |
| 2015/0216739 A1* | 8/2015 | Datwyler | A61F 13/505 | 604/385.14 |
| 2015/0290049 A1* | 10/2015 | Riha-Scott | A61F 13/505 | 604/387 |
| 2015/0374559 A1* | 12/2015 | Fukuzawa | A61F 13/49017 | 604/385.29 |
| 2016/0058631 A1* | 3/2016 | Ormsby | A61F 13/5644 | 604/391 |
| 2016/0151212 A1* | 6/2016 | McCatty | A61F 13/66 | 604/385.14 |
| 2017/0224549 A1* | 8/2017 | Helit | A41B 9/001 | |
| 2019/0046369 A1* | 2/2019 | Allison-Rogers | A61F 13/49006 | |
| 2020/0154790 A1* | 5/2020 | Cleary | A41B 13/04 | |

OTHER PUBLICATIONS

Definition of Mesh (Year: 2020).*
Cloth diaper 101 (Year: 2018).*
Khusainova, Rima, Sewing Glossary: Three Ways to Sew Elastic Waistband Tutorial < https://blog.fabrics-store.com/2018/07/10/sewing-glossary-three-ways-to-sew-elastic-waistband-tutorial/> Jul. 10, 2018 (Year: 2018).*
Apostolides, Anne, Cloth diaper 101—Types of cloth diapers, < https://nerdymommas.com/blogs/news/types-of-cloth-diapers> Aug. 20, 2018 (Year: 2018).*

* cited by examiner

INCONTINENCE PANT AND INCONTINENCE PANT SYSTEM

BACKGROUND OF THE INVENTION

Urinary and fecal incontinence are common and distressing problems that affect quality of life, particularly among the elderly. Incontinence can be caused by a variety of factors, some of which include bladder function, stress, congenital defects, stroke, and aging. While some forms of incontinence are treatable with medication or surgery, other forms are not and therefore must be managed.

Incontinence management can involve fluid containment. In this regard, undergarments have been developed that incorporate materials designed to absorb leaked fluid. Such undergarments rely on close-fitting engagement and positional relationships of absorbent materials with predetermined target areas of likely fluid release. When undergarments shift, such as throughout the course of wearing or at night when sleeping, these absorbent materials tend to move out of engagement and position with their intended target areas and thus are prone to leakage. Once fluid moves beyond these absorbent materials, conventional undergarments have no way to contain the leaked fluid and redirect it back to these materials for absorption. As such, fluid tends to leak outside of these undergarments, defeating the purpose of the undergarment, soiling clothing and bedding, and causing embarrassment and frustration for the afflicted and their loved ones and caregivers.

Accordingly, what is needed is an incontinence garment construction that overcomes the disadvantages of conventional constructions. Such a construction should absorb expelled fluids and prevent leakage without qualification, and while being comfortable to the wearer and offering the option of being washable and reusable.

BRIEF SUMMARY OF THE INVENTION

To achieve the foregoing and other aspects, in one embodiment the present invention provides an incontinence pant construction generally including a main body having a front portion, a back portion, a crotch portion, a waist opening, and two leg openings. An elasticized waist cuff is formed at the waist opening, an elasticized leg cuff is formed at each of the two leg openings, and a suspended mesh lining is disposed within the main body. The suspended mesh lining is attached to each of the elasticized waist cuff and the two elasticized leg cuffs, and each of the cuffs include continuous inner and outer facing portions forming an open-ended pocket therebetween having a pocket depth forming an absorption area containing at least a portion of an absorbent pad.

In some embodiments, the suspended mesh lining may be attached along each of the elasticized waist cuff and the elasticized leg cuffs and is otherwise free of attachment to the main body, and wherein the suspended mesh lining includes at least one access opening therethrough for insertion and removal of at least one absorbent pad positionable between the suspended mesh lining and the main body.

In some embodiments, the at least one access opening may include a first access opening positioned between the elasticized waist cuff and one of the elasticized leg cuffs and a second access opening positioned near the crotch portion, the first access opening for insertion and removal of at least one first absorbent pad to be positioned in any of the front portion, the back portion, side portions or combinations thereof, and the second access opening for insertion and removal of at least one second absorbent pad to be positioned in the crotch portion.

In some embodiments, each of the main body and the suspended mesh may be constructed from waterproof hydrophobic material.

In some embodiments, the crotch portion may be constructed from a single piece of material and is free of seams.

In some embodiments, the incontinence pant may further include at least one removable absorbent pad, at least a portion of which is disposed in the open-ended pocket.

In some embodiments, the inner and outer portions may be stitched together to form a closed pocket adjacent the open-ended pocket, the closed pocket containing an elastic component.

In some embodiments, the incontinence pant may further include a first fastener attached to the suspended mesh lining at the front portion of the main body and a second fastener attached to the suspended mesh lining at the back portion of the main body, each of the first and second fasteners for removably attaching a reusable pocketed sling or a disposable absorbent pad.

In some embodiments, the first and second fasteners may each be concealed beneath an open-sided cuff.

In some embodiments, the pocket depth may be at least 1 inch.

In another embodiment, the present invention provides an incontinence system including an incontinence pant and at least absorbent pad. The absorbent pant includes a main body having a front portion, a back portion, a crotch portion, a waist opening, and two leg openings, an elasticized waist cuff formed at the waist opening, an elasticized leg cuff formed at each of the two leg openings, and a suspended mesh lining disposed within the main body attached at each of the elasticized waist cuff and the two elasticized leg cuffs, wherein each elasticized leg cuff includes continuous inner and outer facing portions forming an open-ended pocket therebetween having a pocket depth of at least 2 inches. The at least one absorbent pad is positionable between and removable from between the suspended mesh lining and the main body.

In some embodiments, the suspended mesh lining may include a first access opening located between the elasticized waist cuff and one of the elasticized leg cuffs and a second access opening located near the crotch portion, the first access opening providing access for insertion and removal of at least one first absorbent pad to be positioned in any of the front portion, the back portion or therebetween, and the second access opening for insertion and removal of at least one second absorbent pad to be positioned in the crotch portion.

In some embodiments, the system may include a disposable absorbent pad positionable in the crotch area and attachable at each of first and second ends to the suspended mesh lining.

In some embodiments, the system may include a reusable sling positionable in the crotch area and attachable at each of first and second ends to the suspended mesh lining, the reusable sling having a pocket for containing a disposable absorbent pad.

In some embodiments, the at least one absorbent pad may include a first absorbent pad positionable between the suspended mesh lining and the main body at any of the front portion, back portion of therebetween, and a second absorbent pad positionable between the suspended mesh lining and the main body at the crotch portion, wherein the first absorbent pad is dimensioned larger than the second absorbent pad.

In another embodiment, the present invention provides an incontinence pant construction generally including a main body having a front portion, a back portion, a crotch portion, a waist opening, and two leg openings. An elasticized waist cuff is formed at the waist opening and an elasticized leg cuff is formed at each of the two leg openings. The incontinence pant may be used alone or over another garment such as a disposable diaper, liner or the like.

Embodiments of the inventive concepts can include one or more or any combination of the above aspects, features and configurations.

BRIEF DESCRIPTION OF THE DRAWINGS

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings.

DETAILED DESCRIPTION OF EXEMPLARY EMBODIMENTS

Figure 1:
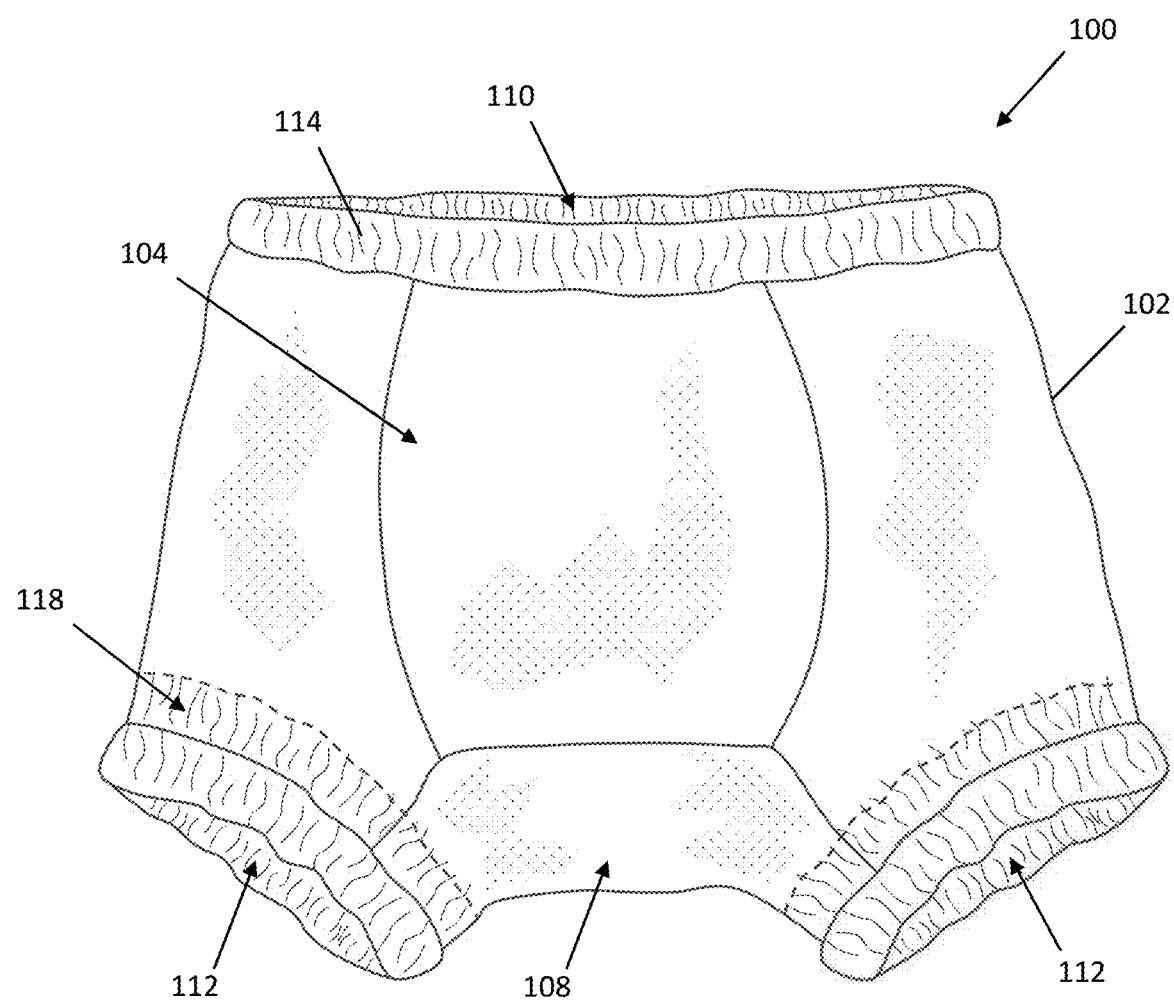
FIG. 1 is a front view of an incontinence pant according to the present disclosure.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. The aspects, features and functions described below in connection with one embodiment are intended to be applicable to the other embodiments described below except where expressly stated or where an aspect, feature or function is incompatible with an embodiment.

Referring to the drawing figures, the inventive concepts disclosed herein are directed to an incontinence pant construction and incontinence pant system compatible for use with different materials and material constructions configured for fluid absorption. Unlike conventional undergarment constructions, the incontinence pant construction disclosed herein is a fluid containment system configured to direct fluid that escapes initial absorption to a containment area for absorption. The incontinence pant and system is reconfigurable in that various absorbent pad types and configurations can be utilized and positioned to suit the specific needs of the wearer. The system further provides reusability and disposability options based on user preference, and some components of the system may be washable and reusable while other components may be disposable. In some embodiments all components may be disposable. In some embodiments all components may be reusable. As used herein, the term disposable includes materials for single use as well as materials capable of withstanding a finite number of washings.

Figure 2:
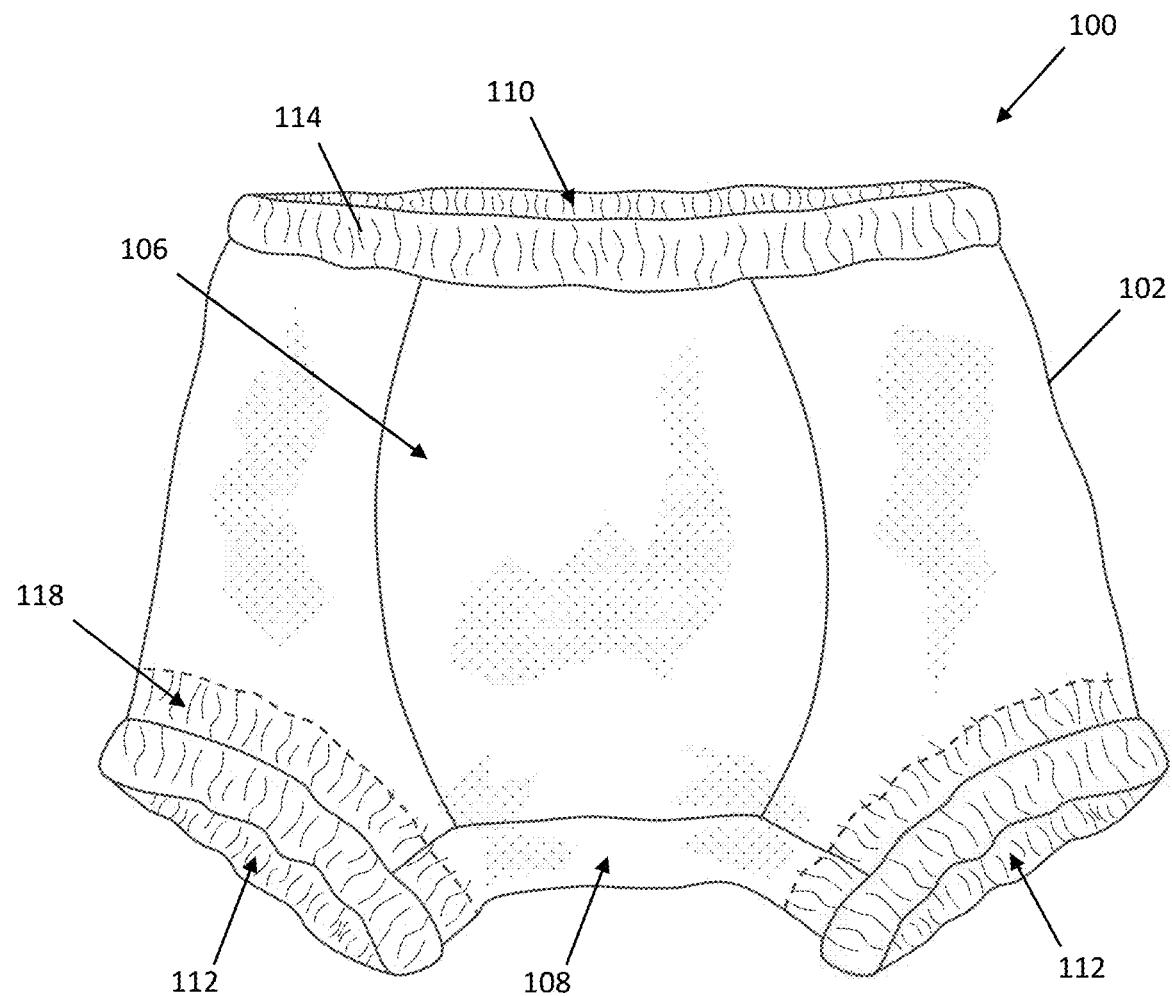
FIG. 2 is a back view of the incontinence pant of FIG. 1.

FIGS. 1 and 2 depict an incontinence pant generally at reference numeral 100. The incontinence pant 100 can be worn as a stand-alone garment, for example while sleeping, or as an undergarment to be worn beneath clothing. The incontinence pant 100 as shown is configured as a short pant; however, it is envisioned and understood that other configurations are possible including briefs, shorts, and pants having a longer leg. The incontinence pant 100 includes a main body 102 having a front panel 104, a back panel 106, a crotch panel 108, a waist opening 110, and two leg openings 112. In some embodiments the main body 102 can be constructed from reusable materials such as waterproof hydrophobic materials including, but not limited to, polyester stretch laminate or the like for comfort, durability and launderability, among other advantages. In some embodiments the main body 102 can be constructed from disposable materials including, but not limited to, disposable non-woven materials.

The main body 102 can be constructed from separate panels sewn, bonded, glued, adhered or otherwise fastened together. In the non-limiting example shown in FIGS. 1 and 2, the main body 102 includes the front panel 104, back panel 106, and crotch panel 108 joined to form the main body. Each of the front panel 104, back panel 106, and crotch panel 108 can comprise one single panel or multiple joined panels. In some embodiments, the crotch panel 108 can be constructed from a single piece of material devoid of seams to prevent fluid leakage common at seams. The crotch panel 108 is preferably wider than conventional crotch widths, and in a particular embodiment can have a width from 6-8 inches, and as shown extends continuously from inner cuff-to-inner cuff and from the front panel 104 to the back panel 106. Reducing seams or eliminating seams from the crotch panel 108 altogether, together with the leg cuff construction discussed further below, functions to direct unabsorbed fluid to an absorption area for absorption by material positioned in the absorption area.

The waist opening 110 includes an elasticized waistband 114, including elasticized material, forming a waistband cuff (see FIGS. 3 and 4 at 116) for tight-fitting engagement around the waist of the user. Each leg opening 112 includes an inner elasticized leg cuff 118 for tight-fitting engagement around a leg of the user. Elastic elements may be disposed within their respective cuff or may be an integral component of the material(s) forming the cuff. Each of the waistband cuff 116 and the two leg cuffs 118 form an absorption area in which unabsorbed fluid (e.g., fluid escaping initial absorption) is contained, collected, and absorbed by an absorbent pad(s) having a portion disposed in the absorption area as discussed further below. Each of the waistband cuff 116 and the two leg cuffs 118 have a predetermined cuff depth or "pocket depth" forming an absorption area. In a non-limiting example, the pocket depth may be at least 1 inch. In some embodiments the pocket depth may be between 1 and 2 inches. In some embodiments the pocket depth may be greater than 2 inches.

Figure 3:
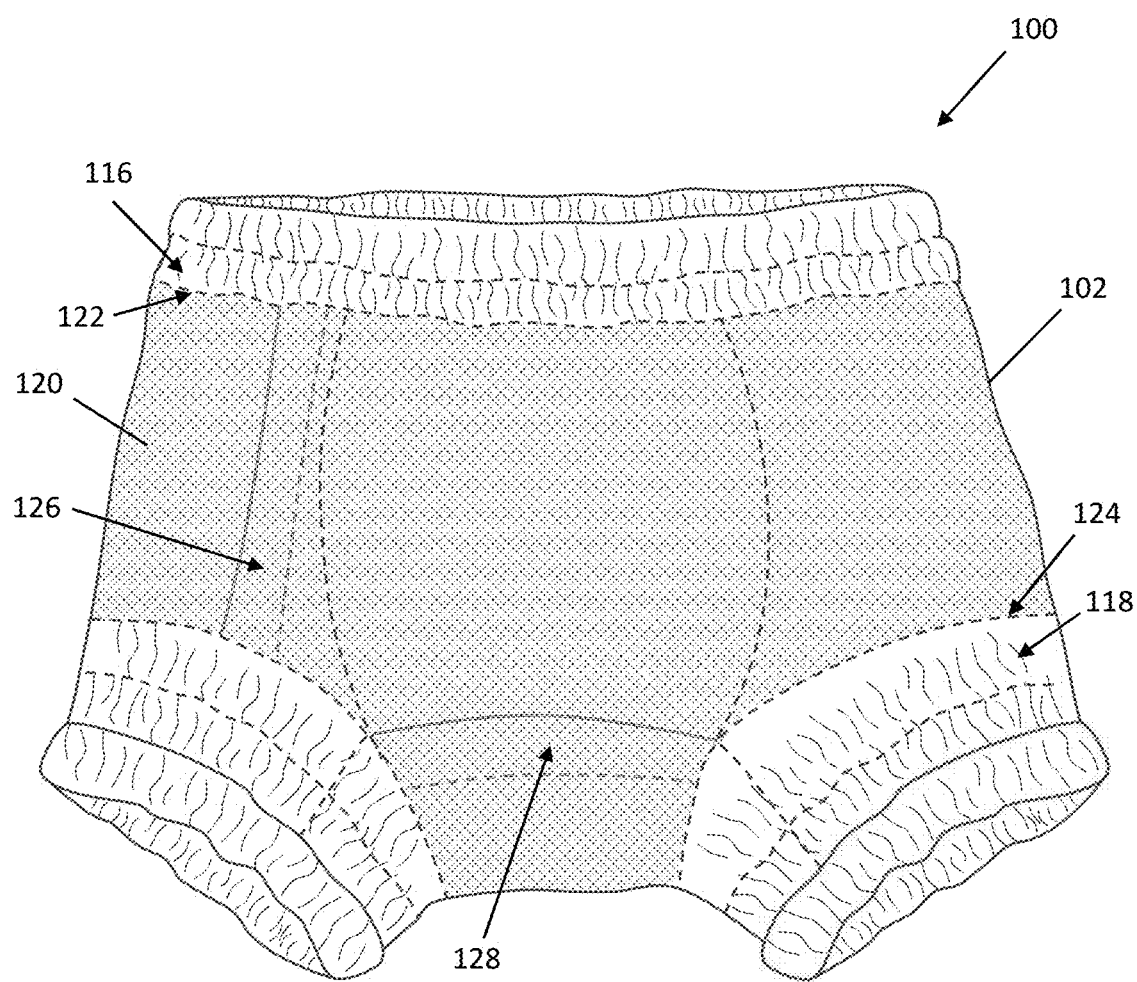
FIG. 3 is a front view of the incontinence pant of FIG. 1 shown turned inside-out to reveal the suspended mesh lining having access openings shown in a closed condition.

FIG. 3 shows the incontinence pant 100 turned inside out to illustrate the cuff constructions and an internal suspended mesh lining 120 secured at the cuffs. The pant 100 may be constructed with or without the mesh lining. The suspended mesh lining 120 covers all or most of the inner surface of the main body 102. The suspended mesh lining 120 may be constructed from polyester mesh, highly absorbent material, etc. The suspended mesh lining 120 can be sewn or otherwise attached to each of the waistband cuff 116 and the two leg cuffs 118 and is otherwise free of attachment to the main body 102. More specifically, the suspended mesh lining 120 can be attached at the waistband to an edge 122 of the waistband cuff 116 and at each leg opening to an edge 124 of the leg cuff 118. Attachment to each of the waistband cuff 116 and the leg cuffs 118 maintains the suspended mesh lining in place relative to the main body, and detachment from the main body at locations other than the aforementioned attachment points provides a continuous annular pocket around the garment between the main body and the mesh lining for strategically positioning one or more absorbent pads under the mesh and within the pocket cuffs for fluid absorption based on any one or more of user need, anatomy, comfort, sleeping or sitting position, fluid absorption needs, etc.

Figure 4:
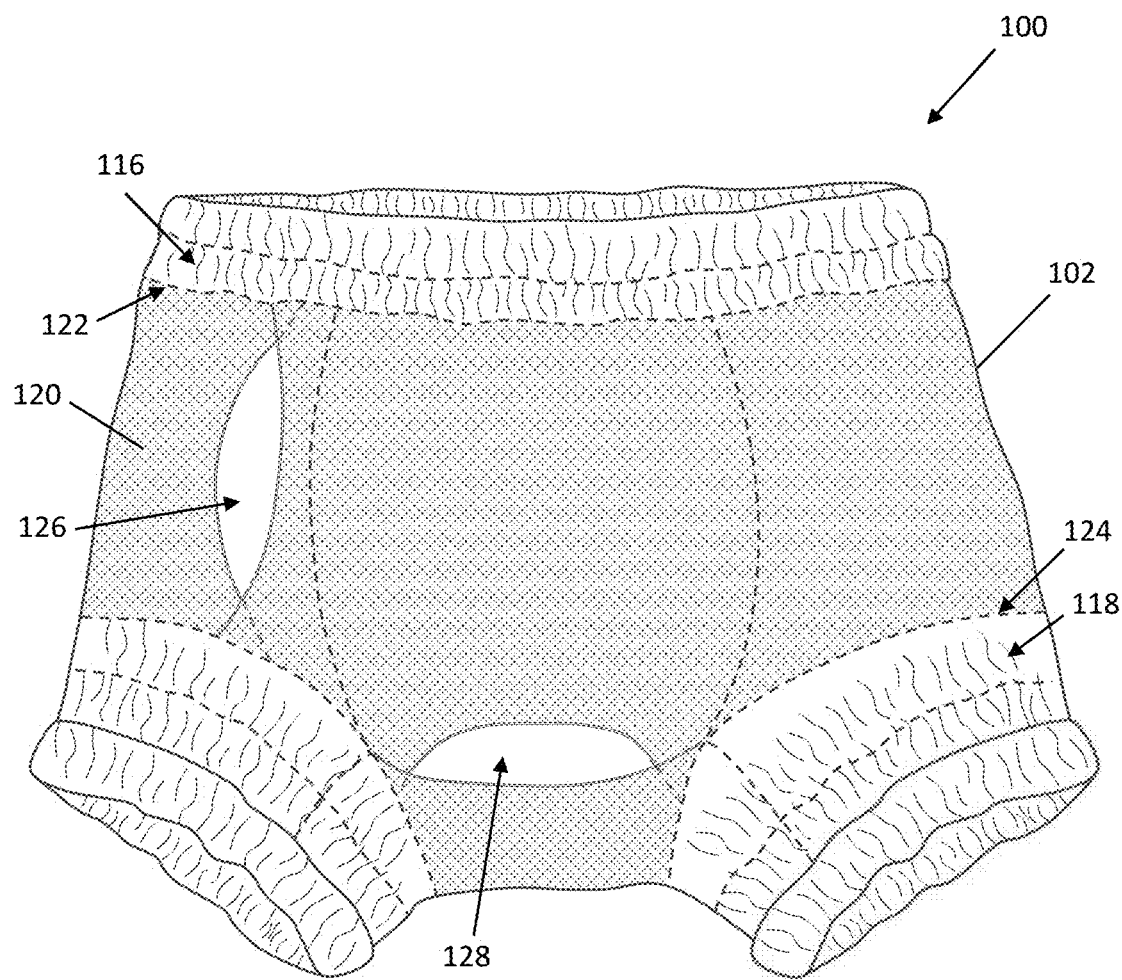
FIG. 4 is a front view of the incontinence pant of FIG. 4 showing the access openings in an open condition.

FIGS. 3 and 4 further illustrate access openings through the suspended mesh lining 120, with FIG. 3 showing the access openings in a closed condition and FIG. 4 showing the access openings in an open condition. The access openings provide access to the interior space between the main body 102 and the suspended mesh lining 120 for insertion and removal of absorbent padding. In some embodiments the access openings include a first or "vertical" elongate opening 126 extending substantially continuously between the waistband cuff 116 and one of the leg cuffs 118, and a second or "horizontal" elongate opening 128 extending substantially continuously between the two leg cuffs 118. The two elongate openings can be dimensioned and oriented as shown or provided in lengths and orientations. Each access opening is generally constructed from overlapping layers of suspended mesh that are pulled apart to provide an unobstructed opening through the mesh lining. The first elongate opening 126 can be sized larger to position large absorbent pads at one or more of the front, back and sides of the garment, while the second elongate opening 130 can be sized smaller to position small pads in the crotch area.

Figure 5:
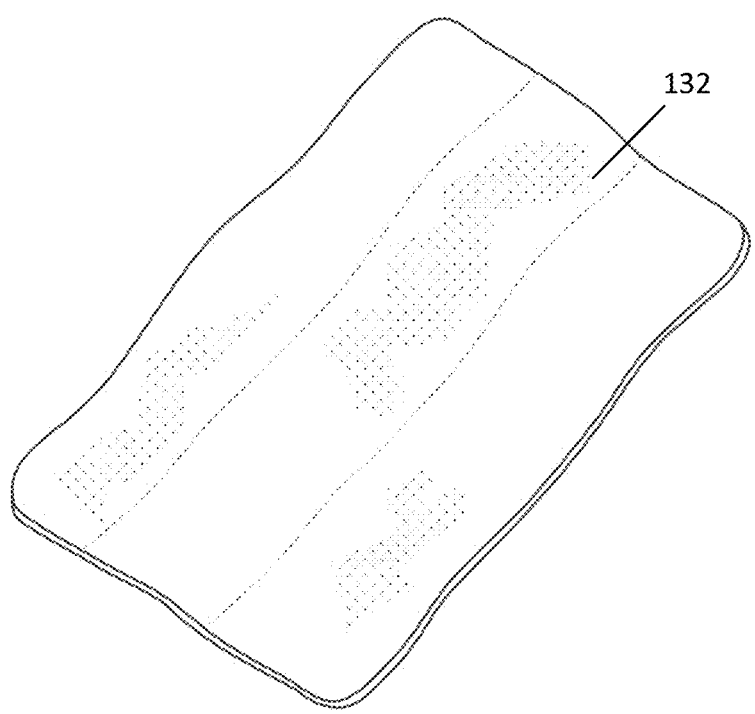
FIG. 5 is a perspective view of a non-limiting example of a large absorbent pad.
Figure 6:
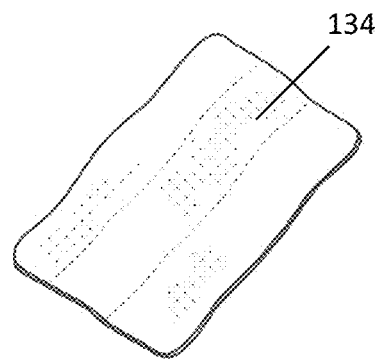
FIG. 6 is a perspective view of a non-limiting example of a small absorbent pad.

FIG. 5 shows a non-limiting example a large absorbent pad 132 for use, for example, at the front, back or sides of the main body 102. FIG. 6 shows a non-limiting example of a small absorbent pad 134 for use, for example, in the crotch area. Combinations of large and small, large and large, and small and small absorbent pads may be used separately or simultaneously in one or more predetermined areas of the garment depending on user need(s). Absorbent pads can include absorbent material encased within or positioned against a backing layer. Absorbent materials can include, but are not limited to, materials having a liquid absorbing function such as polymer materials and the like in disposable constructions and absorbent fibers in reusable constructions.

Figure 7:
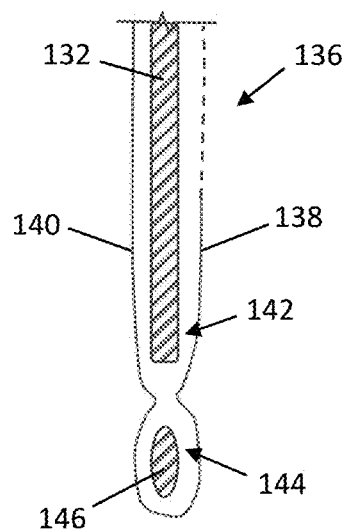
FIG. 7 is a sectional view through a leg cuff forming an open-ended pocket for receiving a portion of an absorbent material.

FIG. 7 shows a cuff pocket construction generally at reference numeral 136. Cuff pockets, formed at the waistband and legs, can be formed by folding over the main body to provide an inner layer 138 facing an outer layer 140 forming an absorption area 142 therebetween for containing a portion of an absorbent material such as a portion of an absorbent pad 132. A second pocket 144 positioned adjacent the cuff pocket can be sewn closed to contain an elastic element 146. The second pocket 144 can be formed by stitching together the facing inner and outer layers 138, 140 of the main body. Fluid escaping initial contact with the absorption pad(s) pad collects in the cuff pocket(s) and is ultimately absorbed by the absorbent pad(s).

Figure 8:
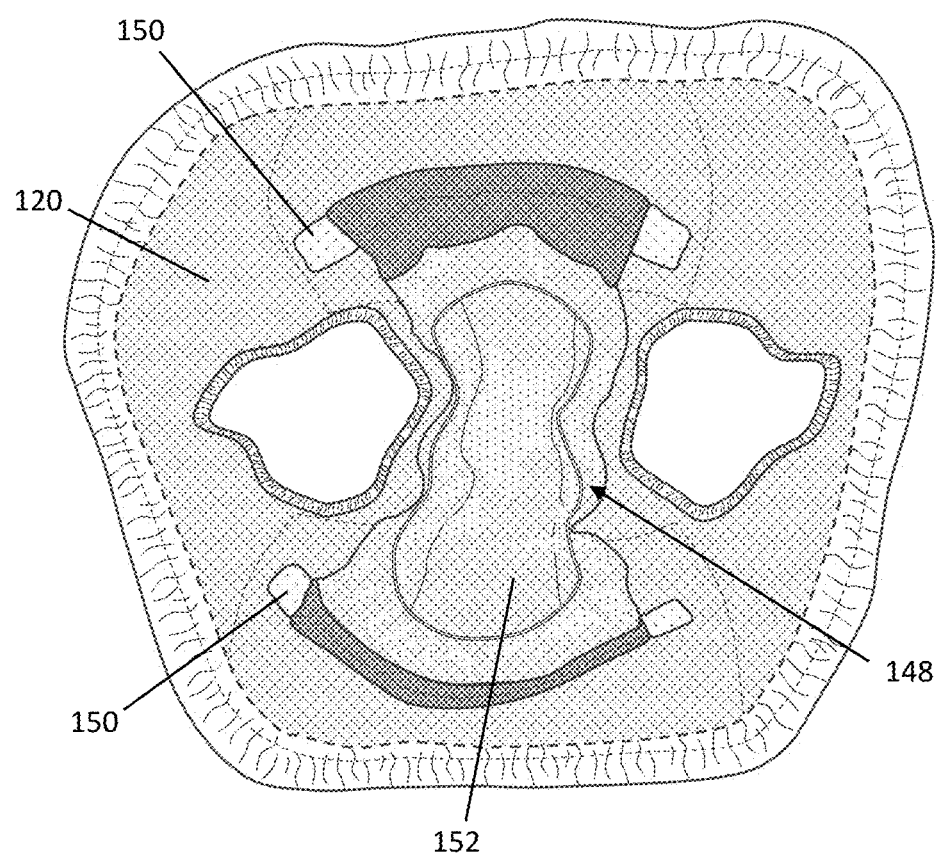
FIG. 8 is a top view into the incontinence pant of FIG. 1 showing an optional pocketed sling installed containing an absorbent pad.
Figure 9:
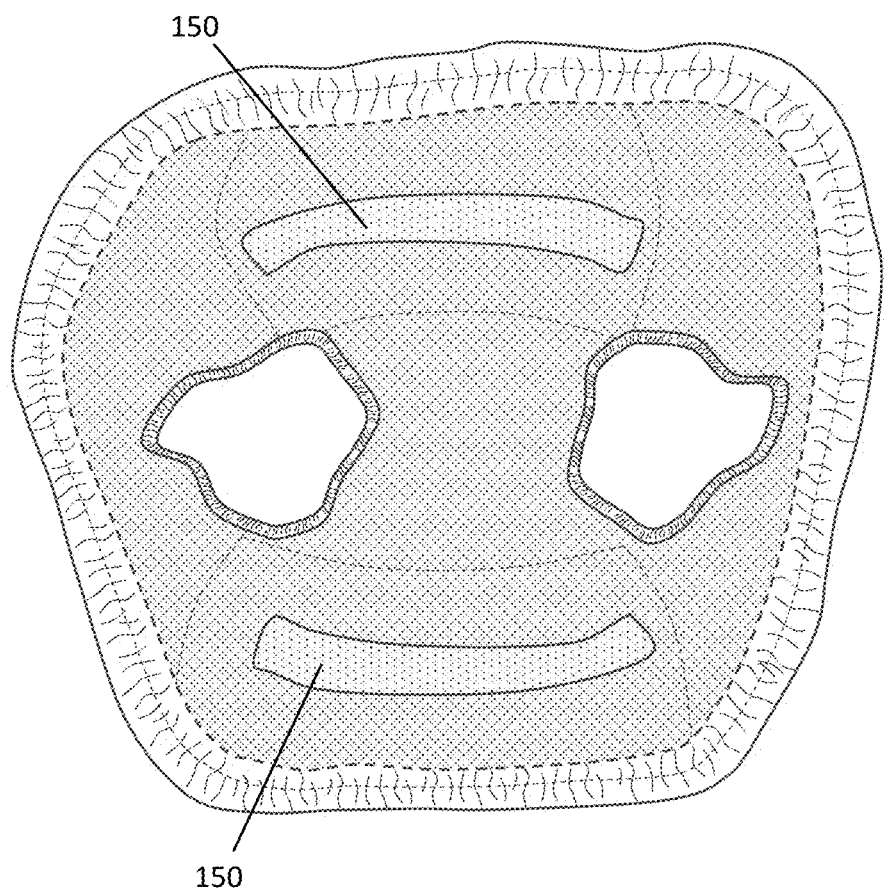
FIG. 9 is a top view into the incontinence pant of FIG. 8 showing the pocketed sling removed to reveal pocketed sling attachment fasteners.

FIG. 8 shows the incontinence system further including an optional absorbent component in the form of a pocketed sling 148 positioned about the crotch area. The pocketed sling 148 can be removably attached at opposing ends to complimentary fasteners 150 affixed to the inside of the suspended mesh lining 120 at the front and back panels. Fasteners can include, but are not limited to, snaps or hook and loop fastener strips wherein the hook components are affixed to the pocketed sling and the loop components are affixed to the mesh lining, or vice versa. In a pant devoid of mesh lining, the fasteners may be affixed to the inside of the main body. Hook and loop fasteners may be provided as elongate strips for securing opposing ends of the pocketed sling 148, leaving the middle portion free of attachment to the mesh lining or main body. The pocketed sling 148 can have an elasticized opening and internal pocket for containing a removable absorbent pad 152. The pocketed sling 148 can be used with or without other absorbent pads positioned between the suspended mesh lining 120 and the main body, inside or outside of the crotch area. The pocketed sling 148 can have a shape generally corresponding to the shape of the crotch area and occupy the space partway along the front and back panels and between the leg openings. The pocketed sling 148 itself can be washable and reusable, while the absorbent pad 152 contained therein can be disposable. In use, the pocketed sling 148 including absorbent pad 152 can serve as the primary fluid absorber, while the mesh lining and/or pad(s) under the lining can serve as the secondary fluid absorber. FIG. 9 shows the pant without the pocketed sling to illustrate the positioning of the elongate fastener strips 150.

Figure 10:
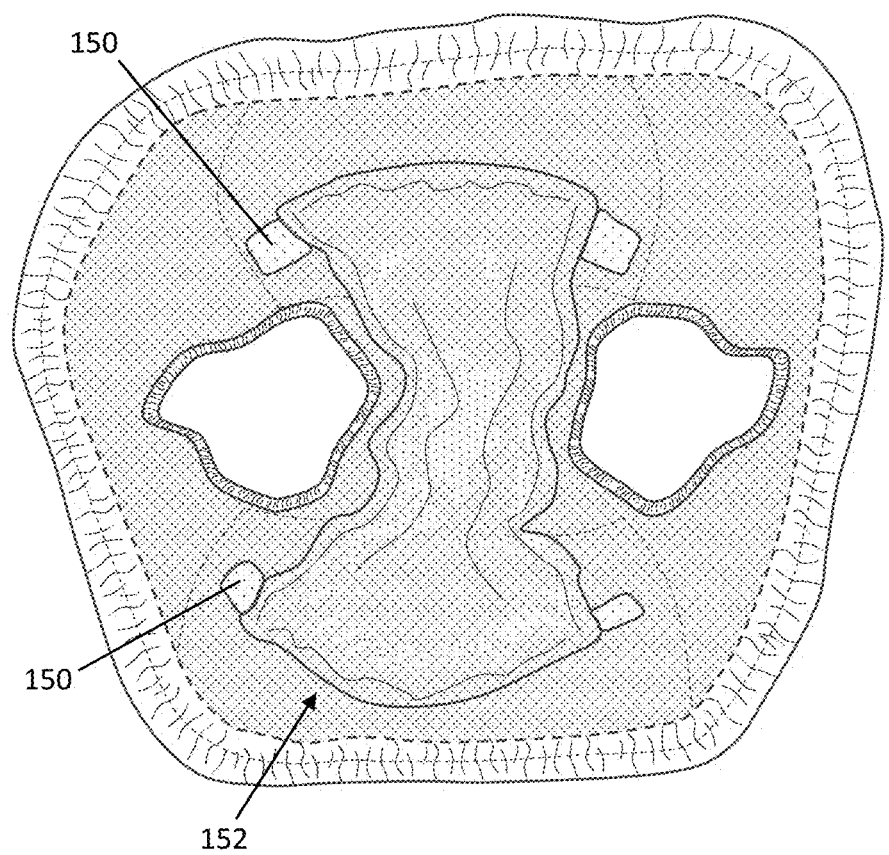
FIG. 10 is a top view into the incontinence pant of FIG. 1 showing an optional disposable absorbent pad installed in the crotch portion.

FIG. 10 shows the incontinence pant system including an optional absorbent component in the form of a disposable sling 152 positioned at the crotch area. The disposable sling 152 be removably attached at opposing ends using fasteners 150. The disposable sling 152 can be constructed from absorbent material and can have a shape generally conforming to shape of the crotch area. The disposable sling 152 can include a fluid-permeable cover layer and fluid-impermeable backing layer with absorbent material therebetween. In use, the disposable sling 152 can serve as the primary absorber for leaked fluid, while the mesh lining and pad(s) beneath serve as the secondary fluid absorber.

Figure 11:
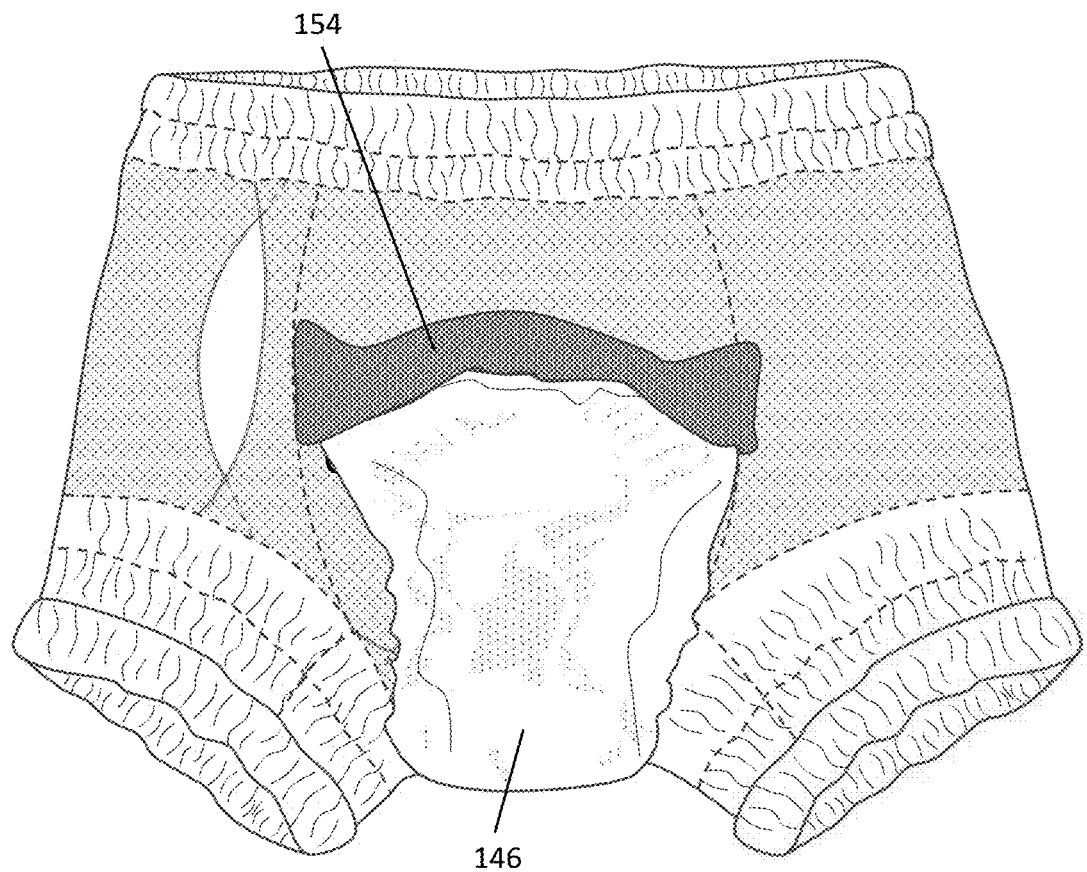
FIG. 11 is a front view of the incontinence pant of FIG. 1 shown turned inside out and with an optional pocketed sling attached positioned at the center front of the pant.
Figure 12:
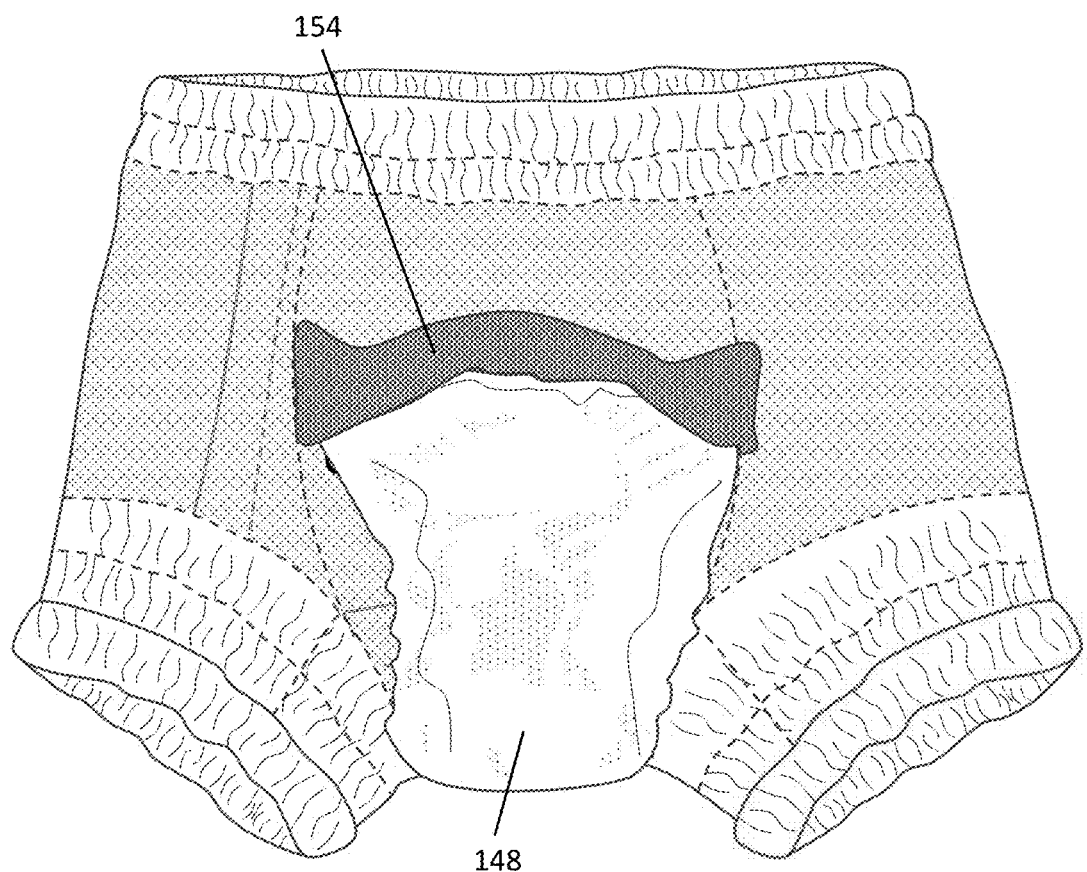
FIG. 12 is a front of the incontinence pant of FIG. 1 shown turned inside out and with an optional disposable absorbent pad installed in the center front of the pant.
Figure 13:
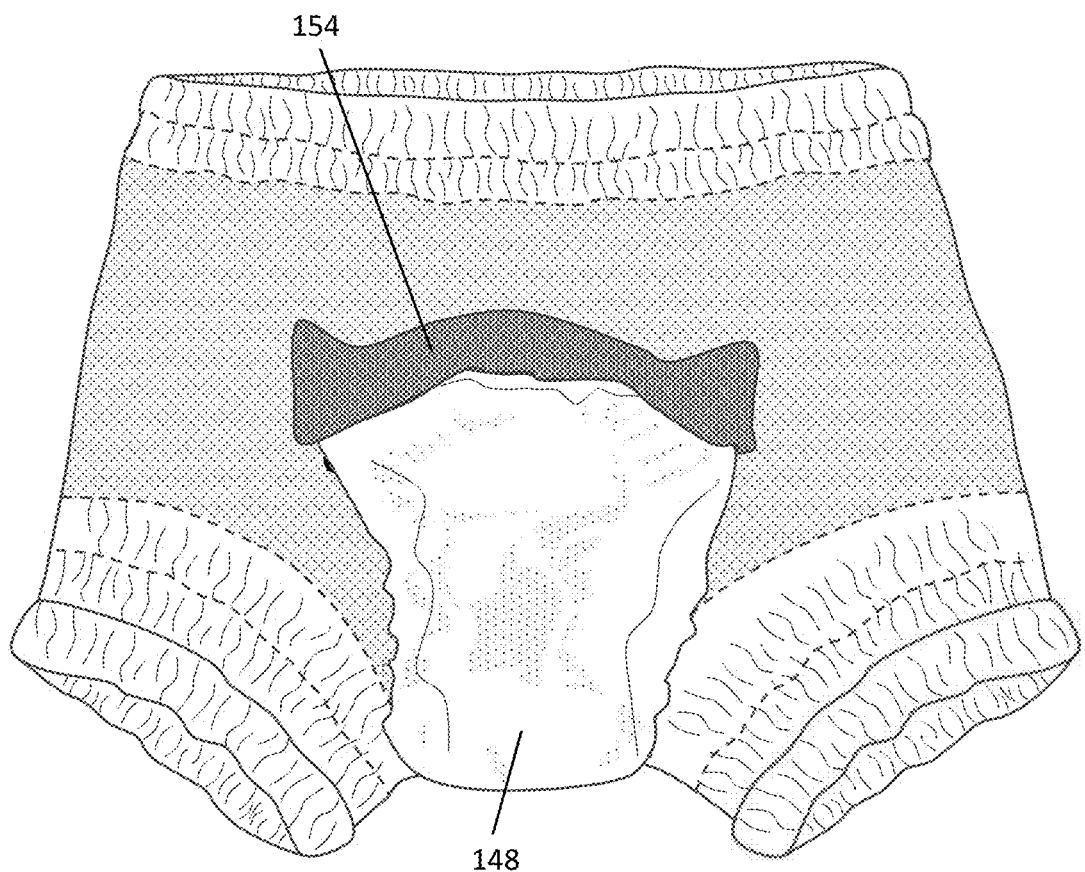
FIG. 13 is a back view of the incontinence pant of FIG. 1 shown turned inside and with an optional pocketed sling or disposable absorbent pad attached positioned at the center back portion.

FIGS. 11-13 show an attached pocketed sling 148. In some embodiments, the fasteners for removably attaching the pocketed sling 148 can be concealed beneath open-sided cuffs 154 pulled to one side to provide access to the underlying fasteners. The pocketed sling 148 is compatible with an incontinence pant having absorbent padding therein as shown in FIGS. 11 and 12, or an incontinence pant without the ability to add absorbent padding therein as shown in FIG. 13.

Figure 14:
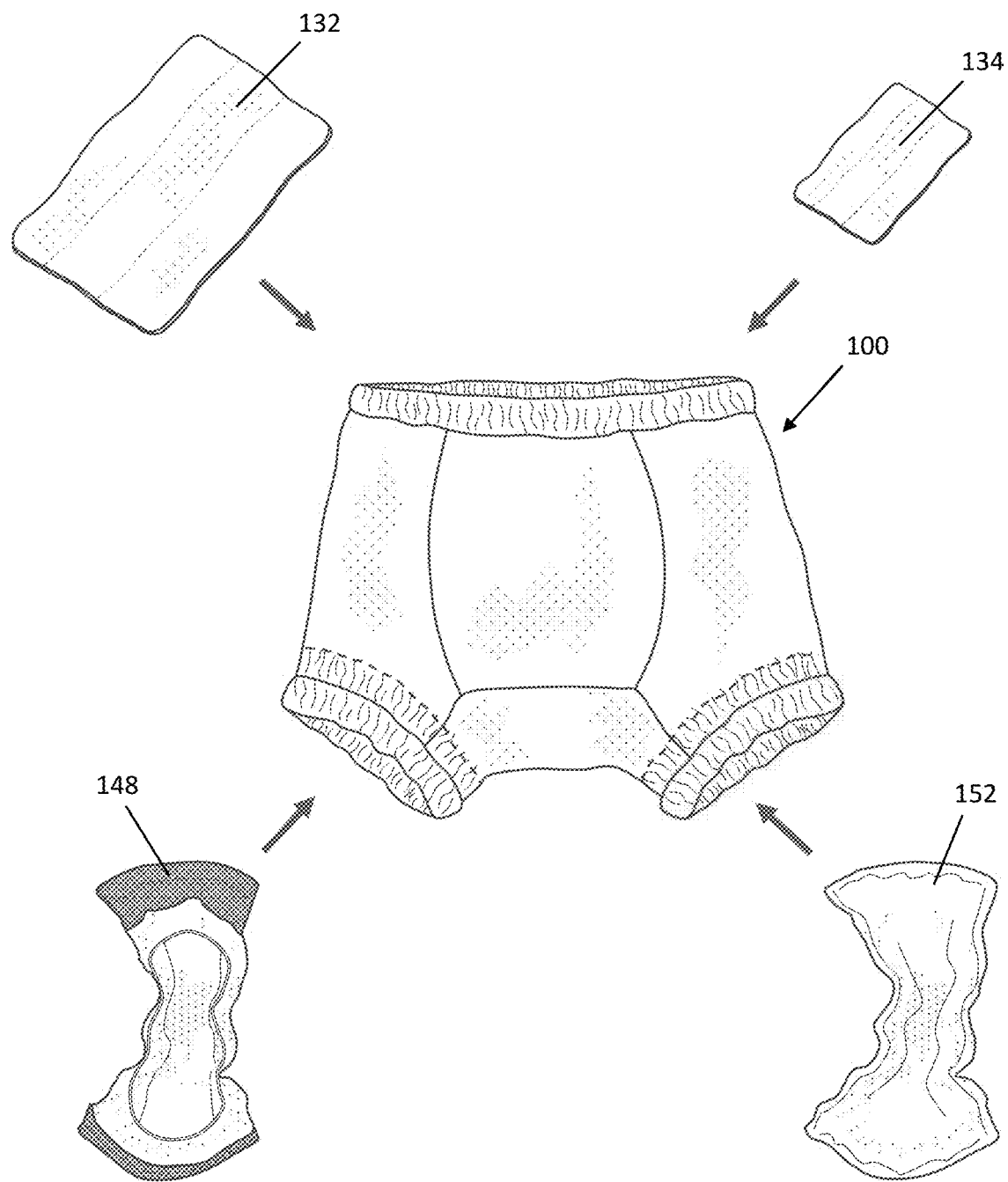
FIG. 14 shows an incontinence system including an incontinence pant for use with compatible absorbent padding and sling constructions.

FIG. 14 shows an incontinence pant system 200 including an incontinence pant 100 having a construction as described herein for use with any one or more of the absorbent padding 132, 134 and slings 148, 152 described herein, depending on user need, anatomy, preference, etc.

Figure 15:
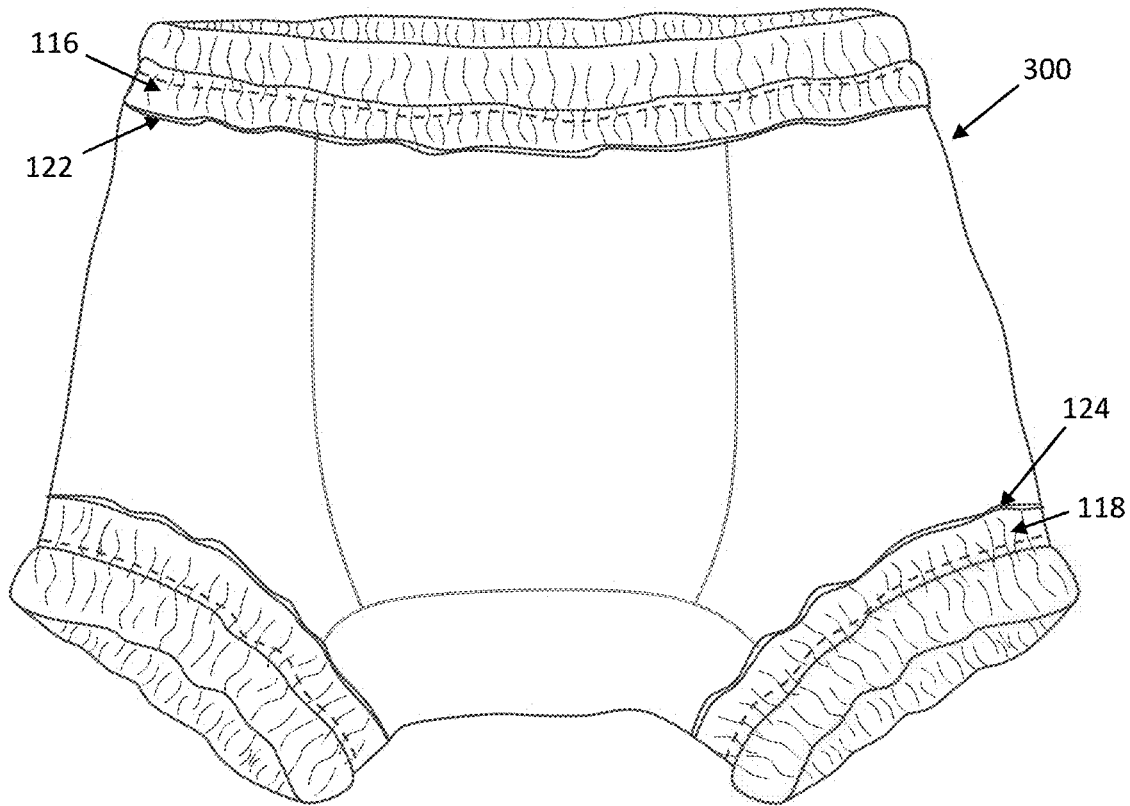
FIG. 15 is a front view of an embodiment of an incontinence pant shown turned inside out and devoid of mesh lining.

FIG. 15 shows another embodiment of an incontinence pant 300 without a mesh lining. The incontinence pant 300 can be worn over a disposable undergarment or used as a standalone garment. The waistband cuff 116 has a free or detached edge 122, while the leg cuffs 118 each have a free or detached edge 124, considering the lack of mesh lining.

While the foregoing description provides embodiments of the invention by way of example only, it is envisioned that other embodiments may perform similar functions and/or achieve similar results. Any and all such equivalent embodiments and examples are within the scope of the present invention and are intended to be covered by the appended claims.

What is claimed is:

1. An incontinence pant, comprising:
   a main body formed as shorts including a pelvis portion and two leg portions, each of the two leg portions extending from the pelvis portion, the pelvis portion forming a waist opening and each of the two leg portions forming a leg opening;
   an elasticized waist cuff formed at the waist opening;
   an elasticized leg cuff formed at each of the leg openings; and
   suspended mesh lining attached within the main body to the elasticized waist cuff and each of the elasticized leg cuffs, the suspended mesh lining free of attachment to the main body except where attached to the elasticized waist cuff and each of the elasticized leg cuffs such that a continuous annular pocket is provided around an interior of the main body formed between the main body and the suspended mesh lining for receiving at least one removable absorbent pad;
   wherein each elasticized leg cuff includes an open-ended cuff pocket formed between folded-over layers of the main body providing a pocket depth of at least 1 inch, each open-ended cuff pocket positioned proximal to a closed pocket containing an elastic element,
   wherein the main body comprises a front panel, a back panel, and a crotch panel joined together to provide a continuous main body, the crotch panel extending continuously between the elasticized leg cuffs such that the crotch panel extends along a portion of the pelvis portion and a portion of each of the leg portions;
   wherein a first access opening for accessing the continuous annular pocket is positioned between one of the elasticized leg cuffs and the elasticized waist cuff and is formed between first and second overlapping portions of the suspended mesh lining;
   wherein a second access opening for accessing the continuous annular pocket is positioned between the elasticized leg cuffs and is formed between overlapping third and fourth portions of the suspended mesh lining.

2. The incontinence pant according to claim 1, wherein the crotch panel has a width between 6 and 8 inches.

3. The incontinence pant according to claim 1, further comprising a first removable absorbent pad positioned within the annular pocket at the first accessing opening, and a second removable absorbent pad positioned within the annular pocket at the second access opening, wherein the second absorbent pad includes portions positioned in each of the elasticized leg cuffs.

4. The incontinence pant according to claim 1, wherein the layers of main body forming the cuff pocket include an inner layer and an outer layer stitched together to form the closed pocket containing an elastic element.

5. The incontinence pant according to claim 1, further comprising a sling removably attached at its opposing ends to the suspended mesh lining.

6. The incontinence pant according to claim 5, further comprising fasteners affixed to the suspended mesh lining for removably attaching the sling, wherein the fasteners are covered with a resilient open-sided cuff.

7. The incontinence pant according to claim 5, wherein the sling includes an internal pocket having an elasticized opening and a removable absorbent pad disposed in the internal pocket.

8. An incontinence system, comprising:
   an incontinence pant comprising:
      a main body formed as shorts including a pelvis portion and two leg portions, each of the two leg portions extending from the pelvis portion, the pelvis portion forming a waist opening and each of the two leg portions forming a leg opening, and the main body having a front portion, a back portion, and a crotch portion;
      an elasticized waist cuff formed at the waist opening;
      an elasticized leg cuff formed at each of the two leg openings;
      suspended mesh lining disposed within the main body, the suspended mesh lining attached at each of the elasticized waist cuff and the two elasticized leg cuffs and the suspended mesh lining free of attachment to the main body other than at the elasticized waist cuff and the two elasticized leg cuffs such that a continuous annular pocket is formed between the suspended mesh lining and the main body;
      a first removable absorbent pad positioned in the continuous annular pocket at the front portion or the back portion of the main body; and
      a second removable absorbent pad, dimensioned smaller than the first removable absorbent pad, positioned in the continuous annular pocket at the crotch portion;
      wherein each elasticized leg cuff includes continuous inner and outer facing portions forming an open-ended pocket therebetween having a pocket depth of at least 1 inch, each open-ended pocket positioned proximal to a closed pocket containing an elastic element;

wherein portions of the second removable absorbent pad are positioned in the open-ended pocket of each of the elasticized leg cuffs;

wherein a first access opening providing access to the continuous annular pocket is positioned between one of the elasticized leg cuffs and the elasticized waist cuff and is formed between first and second overlapping portions of the suspended mesh lining;

wherein a second access opening providing access to the continuous annular pocket is positioned between the elasticized leg cuffs and is formed between overlapping third and fourth portions of the suspended mesh lining; and wherein the crotch portion is constructed from a single panel devoid of seams extending continuously between the elasticized leg cuffs such that the single panel extends along a portion of the pelvis portion and a portion of each of the leg portions.

9. The incontinence system according to claim 8, wherein the second absorbent pad is attachable at each of first and second ends to the suspended mesh lining.

10. The incontinence system according to claim 8, further comprising a reusable sling positionable in the crotch area and attachable at each of first and second ends to the suspended mesh lining, the reusable sling having a pocket for containing a disposable absorbent pad.

11. The incontinence system according to claim 8, wherein each of the main body and the suspended mesh lining is constructed from hydrophobic material, and wherein the crotch portion is constructed from one piece of material.

12. The incontinence system according to claim 8, further comprising a first fastener attached to the suspended mesh lining at the front portion of the main body and a second fastener attached to the suspended mesh lining at the back portion of the main body, each of the first and second fasteners for removably attaching a reusable pocketed sling or a disposable absorbent pad, and the first and second fasteners each concealed beneath an open-sided cuff.

* * * * *